US008182650B2

(12) United States Patent
Tan et al.

(10) Patent No.: US 8,182,650 B2
(45) Date of Patent: *May 22, 2012

(54) MODIFIED KRAFT FIBERS

(75) Inventors: Zheng Tan, Mason, OH (US); Gopal Goyal, Mason, OH (US); Alexander A. Koukoulas, Walpole, MA (US)

(73) Assignee: International Paper Company, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/398,288

(22) Filed: Mar. 5, 2009

(65) Prior Publication Data

US 2009/0165968 A1 Jul. 2, 2009

Related U.S. Application Data

(63) Continuation of application No. 11/582,647, filed on Oct. 18, 2006, now Pat. No. 7,520,958, which is a continuation-in-part of application No. 11/439,659, filed on May 24, 2006.

(60) Provisional application No. 60/684,018, filed on May 24, 2005.

(51) Int. Cl.
*D21C 3/00* (2006.01)
*D21C 1/04* (2006.01)
(52) U.S. Cl. ................. 162/78; 162/17; 162/68; 162/76
(58) Field of Classification Search .................... 162/17, 162/63, 68, 82, 78
See application file for complete search history.

(56) References Cited

U.S. PATENT DOCUMENTS

| 1,831,032 | A |   | 11/1931 | Richter |        |
|-----------|---|---|---------|---------|--------|
| 2,709,699 | A |   | 5/1955  | Wolf    |        |
| 2,801,955 | A |   | 8/1957  | Rutenberg et al. | |
| 2,904,460 | A |   | 9/1959  | Nolan   |        |
| 3,617,431 | A |   | 11/1971 | Croon et al. |   |
| 3,932,209 | A |   | 1/1976  | Chatterjee |     |
| 4,174,997 | A | * | 11/1979 | Richter ......................... 162/19 |
| 4,436,586 | A | * | 3/1984  | Elmore ......................... 162/19 |
| 4,475,984 | A | * | 10/1984 | Cael ............................. 162/76 |
| 4,486,267 | A |   | 12/1984 | Prusas   |       |
| 4,557,800 | A |   | 12/1985 | Kinsley, Jr. |   |
| 4,668,340 | A |   | 5/1987  | Sherman |        |
| 4,806,203 | A |   | 2/1989  | Elton   |        |

(Continued)

FOREIGN PATENT DOCUMENTS

CA 2036311 8/1991

(Continued)

OTHER PUBLICATIONS

Smook, Handbook for Pulp and Paper Technologists, 1992, Angus Wilde Publications, 2nd edition, p. 100, 194, and 206.*

(Continued)

*Primary Examiner* — Anthony Calandra
(74) *Attorney, Agent, or Firm* — Thomas W. Barnes, III; Matthew M. Eslami

(57) ABSTRACT

A method of producing a modified pulp comprising treating wood chips in an extraction process to remove hemicellose to form treated wood chips; and subjecting said treated wood chips to chemical or semichemical pulping to form a modified Kraft pulp wherein the amount of hemicellulose contained in the modified Kraft pulp is from about 5 to about 10% by dry weight of the modified pulp.

16 Claims, 3 Drawing Sheets

Impact of Extraction Time on Amount of Mass Removal

U.S. PATENT DOCUMENTS

| | | | |
|---|---|---|---|
| 4,826,568 A * | 5/1989 | Gratzl | 162/76 |
| 4,997,488 A | 3/1991 | Gould et al. | |
| 5,531,728 A | 7/1996 | Lash | |
| 5,589,033 A | 12/1996 | Tikka et al. | |
| 5,676,795 A | 10/1997 | Wizani et al. | |
| 5,705,369 A | 1/1998 | Torget et al. | |
| 5,766,159 A | 6/1998 | Martin et al. | |
| 5,866,242 A | 2/1999 | Tan et al. | |
| 5,902,454 A | 5/1999 | Nelson | |
| 6,045,545 A | 4/2000 | Vandemoortele et al. | |
| 6,063,982 A | 5/2000 | Martin et al. | |
| 6,103,059 A | 8/2000 | Call | |
| 6,110,323 A | 8/2000 | Marsland | |
| 6,162,961 A | 12/2000 | Tanner et al. | |
| 6,210,801 B1 | 4/2001 | Luo et al. | |
| 6,258,175 B1 | 7/2001 | Lightner | |
| 6,464,832 B2 | 10/2002 | Engelhardt et al. | |
| 6,506,283 B2 | 1/2003 | Henriscon et al. | |
| 6,533,896 B1 | 3/2003 | Tikka et al. | |
| 6,770,168 B1 | 8/2004 | Stigsson | |
| 2002/0017370 A1 | 2/2002 | Henricson et al. | |
| 2003/0093047 A1 | 5/2003 | Nguyen et al. | |
| 2003/0145961 A1 | 8/2003 | Rousu et al. | |
| 2003/0183351 A1 | 10/2003 | Sealey et al. | |
| 2004/0020854 A1 | 2/2004 | Ali et al. | |
| 2004/0200589 A1 | 10/2004 | Herring et al. | |
| 2005/0065336 A1 | 3/2005 | Karstens | |
| 2007/0193706 A1 | 8/2007 | Kirov et al. | |

FOREIGN PATENT DOCUMENTS

| | | |
|---|---|---|
| CA | 2368872 | 10/2000 |
| GB | 1434232 | 5/1976 |
| RU | 2037594 | 6/1995 |
| RU | 2045597 | 10/1995 |
| RU | 2090170 | 9/1997 |
| RU | 2121025 | 10/1998 |
| RU | 2127783 | 3/1999 |
| RU | 2220245 | 7/2003 |
| RU | 2002125519 | 3/2004 |
| RU | 2003111755 | 8/2004 |
| RU | 2248421 | 3/2005 |
| SU | 1606559 | 11/1990 |
| WO | 9425668 | 11/1994 |
| WO | 9508648 | 3/1995 |
| WO | 9739188 | 10/1997 |
| WO | 9947733 | 9/1999 |
| WO | WO0028133 | 5/2000 |
| WO | 0038607 | 7/2000 |
| WO | 0160752 | 8/2001 |
| WO | 0224032 | 3/2002 |
| WO | 03046227 | 6/2003 |
| WO | WO2006127880 | 11/2006 |

OTHER PUBLICATIONS

Van Heiningen, Hemicellulose Extraction and Its Integration in Pulp Production (Part of the Quarterly Forest Products Industry of the Future Quarterly status report for Q1 05) [downloaded from www.p2pays.org], Van Heiningen report is dated Jan. 31, 2005 quarterly report availible Jun. 22, 2005 [downloaded online Oct. 6, 2008], Department of Energy, p. 53-63.*

Smook, Handbook for Pulp and Paper Technologists, 1992, Angus Wilde Publications, 2nd edition, chapter 9, pp. 98-132.*

Rydholm, Pulping Processes, 1965, Interscience Publishing, p. 663-671, 715, 1122-1125.*

Chritos L. and Prior B., Bleaching Response of Sulfite Pulps to Pretreatment with Xylanases, 1997, Biotechnol, Prog, vol. 13, Abstract.

Durbak Irene, Dissolving Pulp Industry, Sep. 1993, Forest Product Laboratory, p. 1-3.

Smook, Handbook for Pulp and Paper Technologiests, 1992 Angus Wilde Publication, 2nd edition, p. 163.

Gullichsen, J. Editor, Chemical Pulping, 1999, Fapet Oy., p. A25-A28.

Ratliff F., the Possible Correlation Between Hemicelluloses and the Physical Properties of Bleached Kraft Pulps, Jun. 1948, Institute of Paper Chemistry, p. 69-76.

Pekarovicova Alexadra et al., Prebleaching kraft pulp by xylanases, the effect of water prehydrolysis, 1992 TAPPI Journal vol. 76, No. 11, whole document.

Obermanne H., A Study of the effect of Hemicelluloses on Beating and Strength of Pulps, Jun. 1934, Institute of Paper Chemistry, p. 51, 67-71.

Syverud K. and Toven K., Swelling Properties of Sulphite Pulps, 2003, Norwegian Pulp and Paper Research Institute, Figure 2 and Figure 3.

Smook, Handbook for Pulp and Paper Technologists, 1992, Angus Wilde Publications, 2nd edition, Chapter 15.

Gullichsen et al., Chemical Pulping 6A, 1999, Fapet Oy. p. A658-659.

Gullichsen et al., Chemical Pulping 6A, 1999, Fapet Oy. p. A573-574.

Smook, Handbook for Pulp and Paper Technologists, 1992, Angus Wilde Publications, 2nd edition, Chapter 13.

* cited by examiner

Figure 1: Impact of Extraction Time on Amount of Mass Removal

MODIFIED KRAFT FIBERS

RELATED PATENT APPLICATIONS

This is a continuation application which claims priority from a of U.S. patent application Ser. No. 11/582,647 filed on Oct. 18, 2006, now U.S. Pat. No. 7,520,958, which is a continuation-in-part of U.S. patent application Ser. No. 11/439,659 filed May 24, 2006 which in turn claims the benefit of U.S. Provisional Patent Application Ser. No. 60/684,018 filed on May 24, 2005.

FIELD OF THE INVENTION

This invention relates to an improved method for manufacturing pulp, pulp manufactured in accordance with this process and paper and paperboard products manufactured from the bleached pulp of this invention. More particularly, this invention relates to improvement in processes for the manufacture of pulps having reduced hemicellulose content which exhibit one or more beneficial properties.

BACKGROUND OF THE INVENTION

Processes for digesting wood chips to form pulps and processes of bleaching pulps and using bleached pulps in the manufacture of paper, paperboard and absorbent products are known. See for example U.S. Pat. Nos. 6,063,982; 5,766,159; 5,902,454 and 6,464,832

SUMMARY OF THE INVENTION

One aspect of this invention relates to a method of producing a modified Kraft pulp for use in paper, paperboard and pulp products comprising:
  treating wood chips with steam, a liquid comprising water or a combination thereof in an extraction process to remove hemicellose to form treated wood chips; and
  subjecting said treated wood chips to kraft pulping to form a modified Kraft pulp wherein the amount of hemicellulose contained in the modified Kraft pulp is from about 5 to about 10% by dry weight of the modified pulp.

Another aspect of this invention relates to a method of producing a modified Kraft pulp comprising treating Kraft pulp, preferably bleached Kraft hardwood pulp, with steam, a liquid comprising water or a combination thereof to extract hemicellulose from the pulp to form a modified Kraft pulp wherein the amount of hemicellulose in the modified Kraft pulp is from about 5 to about 10% by dry weight of the modified pulp.

Another aspect of this invention relates to modified Kraft pulp formed by the processes of this invention. The modified Kraft pulp of this invention exhibits one or more advantages. These advantages include improved drainage which enhances the speed of paper making processes which use the pulp of this invention as compared to unmodified pulps. Such advantages also include higher freeness, enhanced bleachability, de-watering, drying or a combination of two or more of the foregoing as compared to the un-modified Kraft pulp.

Yet another aspect of this invention relates to paper, paperboard, pulp and absorbent products prepared from the modified pulp of this invention.

Still another aspect of this invention relates to a personal hygiene article for absorbing fluids, the article comprising:
  at least one fluid permeable top sheet layer and at least one substantially fluid impermeable back sheet layer; and
  an absorbent sub layer material interposed between the top sheet layer and the back sheet layer, the sub layer material comprising modified pulp of this invention.

DETAIL DESCRIPTION OF THE INVENTION

Figure 1:
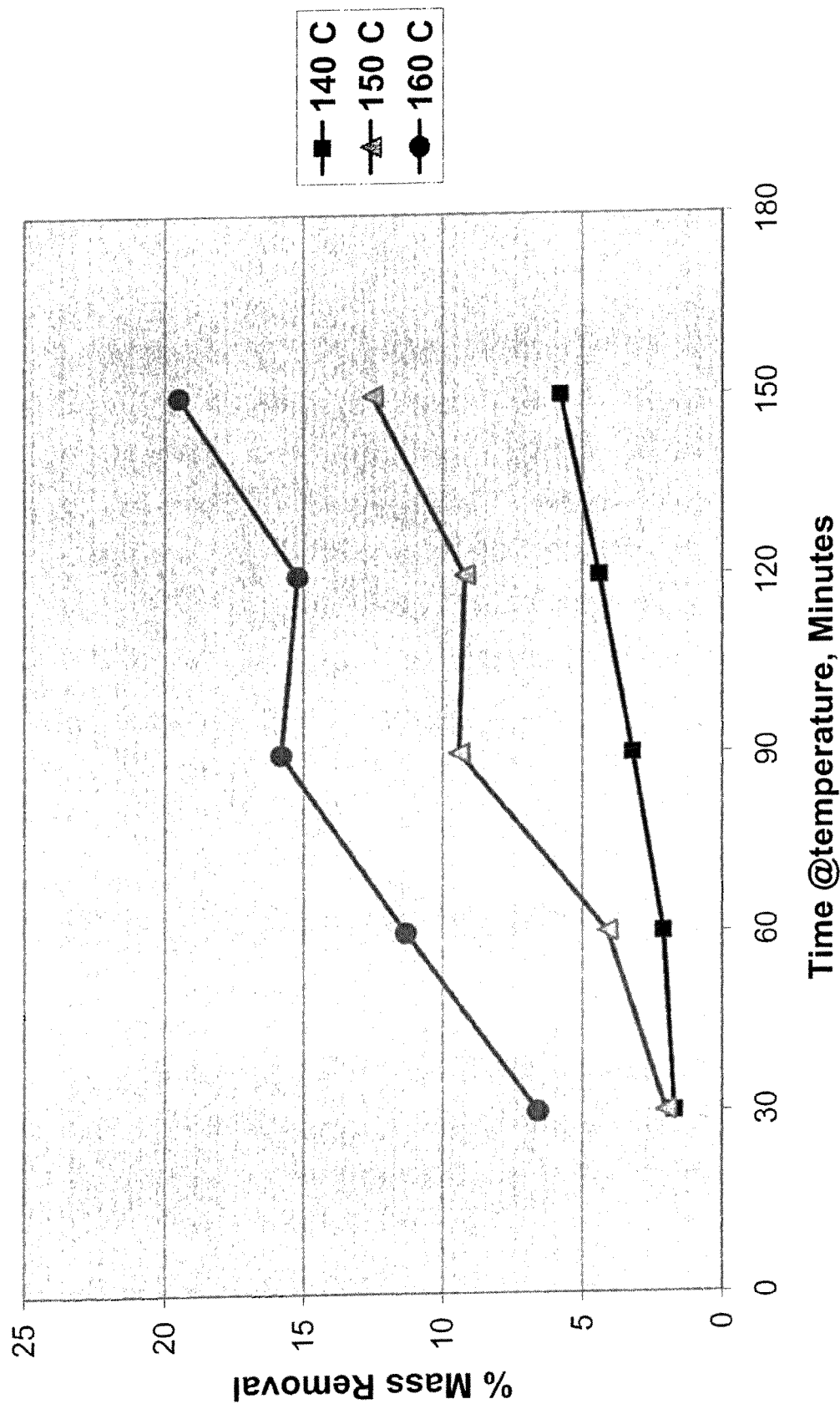
FIG. 1 as a plot of % hemicellulose removed at various temperatures as a function of extraction time.

In the process of this invention wood chips or Kraft pulp are extracted with steam, a liquid comprising water or a combination thereof to reduce and to remove hemicellose to form treated wood chips. The type of wood chips or pulp used in the process of this invention is not critical and wood chips or pulp derived from all types of woods can be used. For example, useful wood chips or pulp include those derived from hardwood trees, softwood trees, or a combination of hardwood and softwood trees. The term "hardwood trees" as used herein refers to deciduous trees (angiosperms) such as aspen and maple, and the term "softwood trees" as used herein refers to coniferous trees (gymnosperms) such as southern pine. In the preferred embodiments of the invention wood chips or pulp derived from hardwoods are used.

The wood chips or pulp are extracted with steam, a liquid comprising water or a combination thereof. In the preferred embodiments of the invention the chips or pulp are extracted with a liquid comprising water. The liquid can consist of water alone or may include one or more additional materials. Such additional materials may vary widely and include organic acids such as acetic acid, propanoic acid, sulfamic acid, lactic acid, citric acid and the like and inorganic acids such as sulfuric acid, sulfurous acids, phosphoric acid, hydrochloric acid, nitric acid, boric acid and the like. Useful additional materials also include inorganic bases such as sodium hydroxide, potassium hydroxide and ammonium hydroxide. Organic and inorganic acids are preferred for use in the practice of this invention and inorganic acids are more preferred.

In the preferred embodiments of this invention the wood chips or pulp are extracted with an aqueous acidic composition to an end pH of less than 7. Use of the aqueous acidic solution allows the extraction to be carried out at lower temperatures as for example at room or ambient temperatures with shorter extraction times. The end pH is preferably equal to or less than about 6, more preferably equal to or less than about 5 and most preferably from about 2 to about 4.

Prior to or during the extraction, the wood chips or Kraft pulp may be treated with hydrogen peroxide (such as hydrogen peroxide, perborate, per carbonate, persulfate, peroxymonosulfuric (or Oxone) or peracetic acid) at an acidic pH (preferably with addition of transition metal catalysts, such as iron, copper, manganese, or cobalt salts). The extracted hemicelluloses (or hydrolyzate) will have a lower molecular weight, and thus a lower solution viscosity at given solids content which enhances the fluidity or ease of pumping extracted hemicelluloses (or hydrolyzate). The catalyzed peroxide treatment may also be applied to the extracted hemicelluloses (hydrolyzate) portion only, achieving the same purpose as above in reducing solution viscosity at given solids content. The outcome of the above processes not only have the advantage of enabling handling higher solids of the extracted hemicelluloses with practical and economical benefits, it also oxidize the carbohydrate structure of hemicelluloses (especially in the case of xylose moieties) which enhances their susceptibility to biological fermentations such as in the biorefinery of the extracted hemicelluloses for ethanol production or the production of other chemicals.

Treatment temperatures may vary widely and any temperature sufficient to form the desired extracted wood chips or Kraft pulp can be used. The treatment temperature is usually at least about 20° C. although lower temperatures may be used if effective to provide the desired treated wood chips or Kraft pulp. The treatment temperature is preferably from about 20° C. to about 200° C., more preferably from about 50° C. to about 190° C. and most preferably from about 100° C. to about 180° C., with a temperature of from about 110° C. to about 170° C. being the temperature in the embodiments of choice.

Treatment times may vary widely and any time sufficient to form the desired treated wood chips or Kraft pulp can be used. The treatment time is usually at least about 5 minutes although longer treatment times may be used if effective to provide the desired lignocellulosic material. The treatment time is preferably from about 5 minutes to about 20 hours, more preferably 15 minutes to about 10 hours and most preferably from about 30 minutes to about 4 hours.

Hemicellulose removed from the extracted wood chips or Kraft pulp can vary widely provided that the amount remaining in the extracted Kraft pulp and modified pulp after Kraft pulping of the extracted wood chips in the second step of the process of this invention is from about 5% to about 10% by dry weight of the modified pulp. For example, the amount of hemicellulose removed in the first step may vary from about 5 by weight or lower to about 20% by weight or higher based on the total amount of hemicellulose in the wood chips or Kraft pulp. In the preferred embodiments of the invention, the amount of hemicellulose removed in the first step may vary from about 10% by weight to about 15% by weight based on the total amount of hemicellulose in the wood chips or Kraft pulp.

The extracted hemicelluloses can be burned in the hog boiler or other types of biomass boilers, such as by spraying onto the biomass fuel feedstock (barks, pin chips, sawdust, coal, etc.), and therefore maintaining the energy balance in the mill. Alternatively, the extracted hemicelluloses can be used as feedstock for fermentation to produce fuel chemicals. The extracted hemicelluloses can be oxidized, or derivatized with ether functional groups or cationic charges. The hemicelluloses thus treated can then be used as papermaking additives, such as added in the paper-machine wet end, or mixed with starch for the use in size-press, or coating. In subsequent Kraft pulping of the extracted wood chips, the extracted hemicelluloses can be diverted away from the pulping process stream, thus reducing the Kraft black liquor recovery boiler heat load (usually being the production capacity bottle-neck).

When wood chips are extracted the treated or extracted wood chips are subject to a chemical or semi chemical pulping process. Such processes are well known to those of skill in the art and will not be described in any great detail. See for example "Handbook for Pulp & Paper Technologies", $2^{nd}$ Edition, G. A. Smook, Angus Wilde Publications (1992) and references cited therein, all of which are herein incorporated by reference. Illustrative of useful chemical and semi-chemical pulping processes are carbonate pulping processes, green liquor pulping processes, Kraft pulping processes or Sulfite pulping processes. Kraft pulping is preferred for use in the practice of this invention.

The amount of hemicellulose contained in the modified Kraft pulp is from about 3 to about 15% by dry weight of the modified pulp. The amount of hemicellulose contained in the modified Kraft pulp is preferably from about 4 to about 13% by dry weight of the modified pulp. The amount of hemicellulose contained in the modified Kraft pulp is more preferably from about 5 to about 10% by dry weight of the modified pulp and is most preferably from about 6 to about 8% by dry weight of the modified pulp. This modified Kraft pulp (either hardwood or softwood) displays significantly higher brightness and paper bulk with improved drainage and drying potential, as compared to the unmodified pulp.

In a preferred embodiment of this invention, the modified Kraft pulp of this invention contains at least about 1% by weight less hemicelluloses of the same pulp when unmodified. In these preferred embodiments of the invention, the modified Kraft pulp contains from about 1% to about 20% by weight less hemicelluloses than the same pulp when unmodified. In these preferred embodiments of the invention, the modified Kraft pulp contains from about 1% to about 20% by weight less hemicelluloses than the same pulp when unmodified. In these preferred embodiments of the invention, the modified Kraft pulp preferably contains from about 1% to about 16% by weight less hemicelluloses than the same pulp when un-modified. In these preferred embodiments of the invention, the modified Kraft pulp more preferably contains from about 2% to about 16% by weight less hemicelluloses than the same pulp when un-modified. In these preferred embodiments of the invention, the modified Kraft pulp most preferably contains from about 2% to about 8% by weight less hemicelluloses than the same pulp when unmodified In the preferred embodiments of the invention, the modified pulp of this invention exhibits higher freeness as measured by the procedure of T227 om-99. The increase in freeness is preferably at least about 20 CSF units greater than that of the unmodified pulp. In the more preferred embodiments of the invention the increase in freeness is at least about 50 CSF units greater than that of the unmodified pulp and in the most preferred embodiments of the invention the increase in from about 50 to about 200 CSF units greater than that of the unmodified pulp.

In the preferred embodiments of the invention the modified pulp of this invention exhibits reduced water retention values (WRV) (as measured by the procedure described in the Examples below) as compared to the unmodified pulp. In these preferred embodiments of the invention, the reduction in water retention is preferably equal to or greater than about 0.1 g/g. In the more preferred embodiments of the invention, the reduction in water retention is preferably equal to or greater than about 0.15 g/g. and in the most preferred embodiments of the invention, the reduction in water retention is equal to or greater than about 0.2 g/g. In the embodiments of choice, the reduction in water retention is from about 0.2 g/g to about 0.5 g/g.

The modified pulp of this invention can be subjected to one or more post pulping treatments as for example beaching with conventional bleaching agents such as chlorine dioxide, elemental chlorine, ozone and peroxide using procedures and apparatuses described in "Handbook For Pulp & Paper Technologies", $2^{nd}$ Edition, G. A. Smook, Angus Wilde Publications (1992) and references cited therein. The pulp can also be subjected to extraction as for example oxygen delignification or extraction with base preferably in the presence of peroxide. In the preferred embodiments of the invention, the modified pulp of this invention exhibits improved bleachability. A benefit of improved bleachability is that the amount of bleaching chemical dose (kappa factor) used can be reduced while reaching the same brightness as the unmodified bleached pulp, thus generating chemical cost savings. Another benefit of improved bleachability is the same amount of bleaching chemical as the unmodified pulp case can be used, especially in early bleaching stages, thus reducing the number of bleaching stages (savings in capital and energy) required to reach the same brightness. Yet another benefit of improved bleachability is that very high brightness pulp can be produced, which cannot be practically achieved with unmodified pulp. For instance, it is well-known fact that Kraft pulp cannot be bleached practically beyond an 89 ISO brightness with a reasonable amount of bleaching agent such as chlorine dioxide. With this modified Kraft pulp, however, high brightness levels equal to or greater than about 90 ISO brightness and preferably from about 90 to about 95 ISO brightness can be achieved in the preferred embodiments of the invention with practical amounts of bleaching chemicals.

In other preferred embodiment of this invention the modified pulp has less anionic charge or less hydrated fiber surface, showing better affinity for paper chemicals such as sizing, dyes and optical brighteners. In another preferred embodiment of this invention the modified Kraft pulp, containing less hemicellulose, has less moisture sensitivity and shows improved performance in hydroexpansivity.

The modified pulp of this invention can be used in the manufacture of pulp products as for example fluff pulp. The modified pulp of this invention can be used in the manufacture of paper and packaging products such as printing, writing, publication and cover papers and paperboard products. Illustrative of these products and processes for their manufacture are those described in U.S. Pat. Nos. 5,902,454 and 6,464,832.

In paper or paperboard making process, the modified pulp of this invention can be used with no or little refining, and the modified pulp can be mixed with fully-refined unmodified pulps, especially unmodified softwood pulps such as Southern Pine pulp, prior to use in paper or paperboard manufacture in various amounts depending on the type of paper. For example, mixtures of the modified pulp of this invention and unmodified softwood pulp can, for example, contain from about 10 to about 90% by weight of modified hardwood pulp of this invention, preferably from about to about 85% by weight of modified hardwood pulp of this invention and more preferably from about 20 to about 80% by weight of modified hardwood pulp of this invention, based on the total weight of the pulp mixture.

The modified pulp of this invention or pulp mixtures comprising the modified pulp of this invention is formulated into an aqueous paper making stock furnish which also comprises one of more additives which impart or enhance specific sheet properties or which control other process parameters. Illustrative of such additives is alum which is used to control pH, fix additives onto pulp fibers and improve retention of the pulp fibers on the paper making machine. Other aluminum based chemicals which may be added to the furnish are sodium aluminate, poly aluminum silicate sulfate and poly aluminum chloride. Other wet end chemicals which may be included in the paper making stock furnish for conventional purposes are acid and bases, sizing agents, dry-strength resins, wet strength resins, fillers, coloring materials, retention aids, fiber flocculants, defoamers, drainage aids, optical brighteners, pitch control chemicals, slimicides, biocides, specialty chemicals such as corrosion inhibitors, flame proofing and anti-tarnish chemicals, and the like. Methods and procedures for formulating mechanical bleached pulp, aluminum based wet end chemicals and other optional wet end chemicals are well known in the art and will not be described in any great detail. See for example, "Handbook For Pulp & Paper Technologies", $2^{nd}$ Edition, G. A. Smook, Angus Wilde Publications (1992) and references cited therein, all of which are herein incorporated by reference.

The aqueous paper making stock furnish comprising the bleached mechanical pulp and the aluminum based compounds is deposited onto the forming wire of a conventional paper making machine to form a wet deposited web of paper or paperboard and the wet deposited web of paper or paperboard is dried to form a dried web of paper or paperboard. Paper making machines and the use of same to make paper are well known in the art and will not be described in any great detail. See for example, *Handbook For Pulp & Paper Technologies*, supra. By way of example, the aqueous paper making stock furnish containing pulp, aluminum based and other optional additives and usually having a consistency of from about 0.3% to about 1% is deposited from the head box of a suitable paper making machine as for example a twin or single wire Fourdrinier machine. The deposited paper making stock furnish is dewatered by vacuum in the forming section. The dewatered furnish is conveyed from the forming section to the press section on specially-constructed felts through a series of roll press nips which removes water and consolidates the wet web of paper and thereafter to the dryer section where the wet web of paper is dried to form the dried web of paper of this invention. After drying, the dried web of paper may be optionally subjected to several dry end operations such as and various surface treatments such as coating, and sizing and calendering.

In the preferred embodiments of this invention, modified pulp forms paper products which exhibit a bulk which is greater than that exhibited by the same or substantially the same pulp when unmodified. Bulk is equal to caliper divided by the basis weight. Basis weight can be determined by the procedure of T410 om-02 and caliper can be determined by the procedure of T411 om-05. In these preferred embodiments of the invention modified pulp forms paper products which exhibit a bulk which is at least about 2% greater than that exhibited by the same or substantially the same pulp when unmodified. In these preferred embodiments of the invention modified pulp forms paper products which exhibit a bulk which is preferably at least about 5% greater than that exhibited by the same or substantially the same pulp when unmodified. In these preferred embodiments of the invention modified pulp forms paper products which exhibit a bulk which is more preferably from about 5% to about 40% greater than that exhibited by the same or substantially the same pulp when unmodified. In these preferred embodiments of the invention modified pulp forms paper products which exhibit a bulk which is most preferably from about 5% to about 30% greater than that exhibited by the same or substantially the same pulp when unmodified.

The paper manufactured in accordance with this invention can be used for conventional purposes. For example, the paper is useful as printing paper, publication paper, newsprint and the like.

For example the modified pulp of this invention can be used prepared absorbent articles as for example diapers, tissues, towels, personal hygiene products using conventional processes. Such products and their methods of manufacture are known to those of skill in the art and will not be described in detail. See for example, U.S. Pat. Nos. 6,063,982 and 5,766,159 and references described therein. The modified pulp of this invention can be used to make saturating kraft paper. Saturating kraft paper is a paper sheet made from unbleached kraft pulp (mixture of mostly hardwood and some softwood such as southern pine) that is used as substrate for impregnation and curing with resin polymers. Saturating kraft paper is used as home and office building materials, such as kitchen counter tops.

The present invention will be described with references to the following examples. The examples are intended to be illustrative and the invention is not limited to the materials, conditions or process parameters set forth in the examples.

Example 1

Northern hardwood chips (predominantly maple), was extracted with water at 160° C. Process conditions and % mass removal are set forth in the following Table I and FIG. 1.

TABLE I

| Exp. No. | Extraction Time (min.) | Extraction Temperature | pH of Extracted Hemicellulose | % mass removal |
|---|---|---|---|---|
| 1 | 30 | 140° C. | 5.16 | 1.7 |
| 2 | 60 | 140° C. | 4.95 | 2.1 |
| 3 | 90 | 140° C. | 5.15 | 3.2 |
| 4 | 120 | 140° C. | 4.98 | 4.4 |
| 5 | 150 | 140° C. | 3.87 | 5.8 |
| 6 | 30 | 150° C. | 4.46 | 2.0 |
| 7 | 60 | 150° C. | 4.07 | 4.1 |
| 8 | 90 | 150° C. | 4.15 | 9.4 |
| 9 | 120 | 150° C. | 3.95 | 9.2 |
| 10 | 150 | 150° C. | 3.55 | 12.5 |
| 11 | 30 | 160° C. | 3.90 | 6.6 |
| 12 | 60 | 160° C. | 3.60 | 11.3 |
| 13 | 90 | 160° C. | 3.55 | 15.8 |
| 14 | 120 | 160° C. | 3.49 | 15.2 |
| 15 | 150 | 160° C. | 3.38 | 19.5 |

The extracted chips were then cooked by Kraft pulping to Kappa number 25. As control, the un-extracted chips were also Kraft cooked to reach a target Kappa number of 25. Both the treated pulps and the control pulps were bleached by the sequences as shown in Table II below.

TABLE II

| | Bleaching Sequences |
|---|---|
| Brown stock | Extracted/Kraft-cooked-kappa 25; Control/Kraft-cooked-kappa 25 |
| Do stage | Kappa factor 0.08 for treated pulp (0.76% $ClO_2$ applied on pulp) Kappa factor 0.08 for control pulp (0.76% $ClO_2$ applied) Kappa factor 0.14 for control pulp (1.33% $ClO_2$ applied) 40 minutes at 50° C., consistency 4% |
| Eop Stage | 90 minutes at 75° C., consistency 10%, 0.4% $H_2O_2$ applied, 1.36% NaOH applied, $O_2$ pressure 60 psi. |
| D1 Stage | 3 hours at 62° C., consistency 10%, 0.73% $ClO_2$ applied, 0.3% NaOH applied on pulp. |
| Ep Stage | 60 minutes at 75° C., consistency 10%, 0.16% $H_2O_2$ applied, 0.46% NaOH applied on pulp. |
| D2 Stage | 3.5 hours at 78° C., consistency 10%, 0.21% $ClO_2$ applied on pulp. |

The brightness results are set forth in Table III below.

TABLE III

| | Brightness | | |
|---|---|---|---|
| | Treated Pulp-Kappa factor 0.08 in Do | Control Pulp-Kappa factor 0.08 in Do | Control Pulp-Kappa factor 0.14 in Do |
| Brown stock | 28.2 | 21.4 | 21.4 |
| After $D_o$ | 35.1 | 26.3 | 36.5 |
| After Eop | 62.1 (P#*3.3) | 40.3 (P#7.1) | 59.2 (P#4.1) |
| After $D_1$ | 84.1 | 68 | 80.5 |
| After Ep | 87.5 | 70.8 | 83.9 |
| After $D_2$ | 91.8 | 82.4 | 89.5 |

*Permanganate Number

It is obvious that the treated pulp can be bleached much easily. In this example, the savings in $ClO_2$ dose is more than 11 lb per ton of pulp production. This is very significant economical benefit. Moreover, this also indicates that if a "normal" dose of $ClO_2$ is used in the $D^o$ stage (i.e., kappa factor of 0.14 to 0.2) for the modified Kraft pulp, a very high brightness pulp (much above the traditional pulp brightness ceiling of ~90 ISO Brightness) can be made. In fact, a very high brightness pulp can be used in the manufacture of high brightness papers and saving optical brightener usage.

Example 2

The modified pulp and the control pulp, which had been bleached with the same dose of $ClO_2$ bleaching chemicals as in Example 1, were refined to various level of freeness. The bulk was determined by the procedures above and the smoothness was determined by the procedure of T538 om-01 (TIP#202). The water retention was determined using the following equipment and procedure.

I. Equipment:
 1. Laboratory centrifuge with free swinging head
 2. Centrifuge cups
 3. filter tubes with fine mesh screens (100 mesh) and screw caps—Custom made (WRV cells)
 4. 2-Liter Vacuum flask with rubber adapter to fit centrifuge cups
 5. Rubber tipped glass rod or equivalent
 6. Beaker, 250 ml
 7. Weighing balance
 8. Indelible pencil
 9. Drying oven (105° C.)
 10. Dissector jar II. Procedure:
 1. Determine consistency of pulp sample(s) and weight out enough to provide 1 gram of bone-dry fiber per sample.
 2. Carefully place sample in beaker and dilute with distilled water to about 0.5% consistency.
 3. Mount WRV cell on filter flask. While swirling the sample, pour enough into the cell to nearly fill it. Apply vacuum until most water is drained, but do not pull air through the pad. Repeat filling and draining until all fiber is on the pad, and most of the water is drained. Use spatula; if necessary get all fiber on the mat.
 4. Do the same with another WRV cell and some of the same pulp (duplicate).
 5. Place WRV cells in centrifuge, and spin at 2000 rpm for 30 minutes.
 6. Remove the plugs, and label the plugs with an indelible pencil.
 7. Weigh wet plugs and record weights.
 8. Dry plugs at 105° C. for four hours.
 9. Weigh dry plug in a hot balance. Record dry weight.

Figure 2:
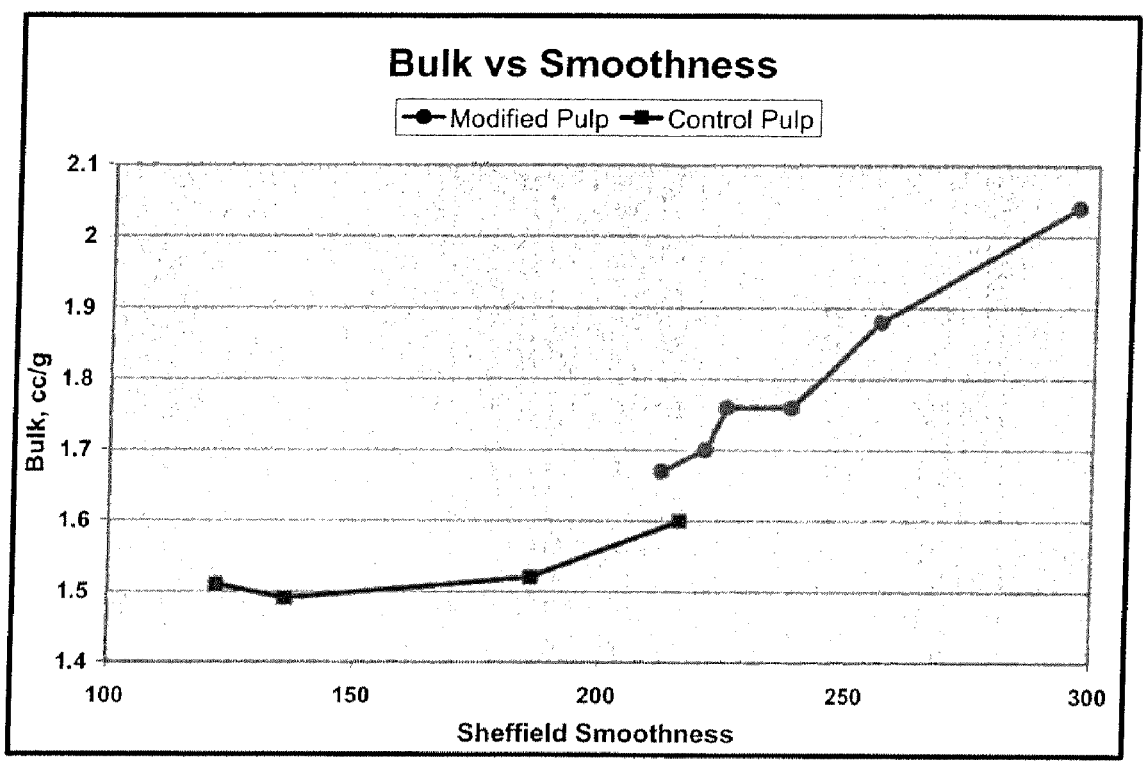
FIG. 2 is a plot of water retention versus freeness for the modified pulp of this invention and the same unmodified pulp.
Figure 3:
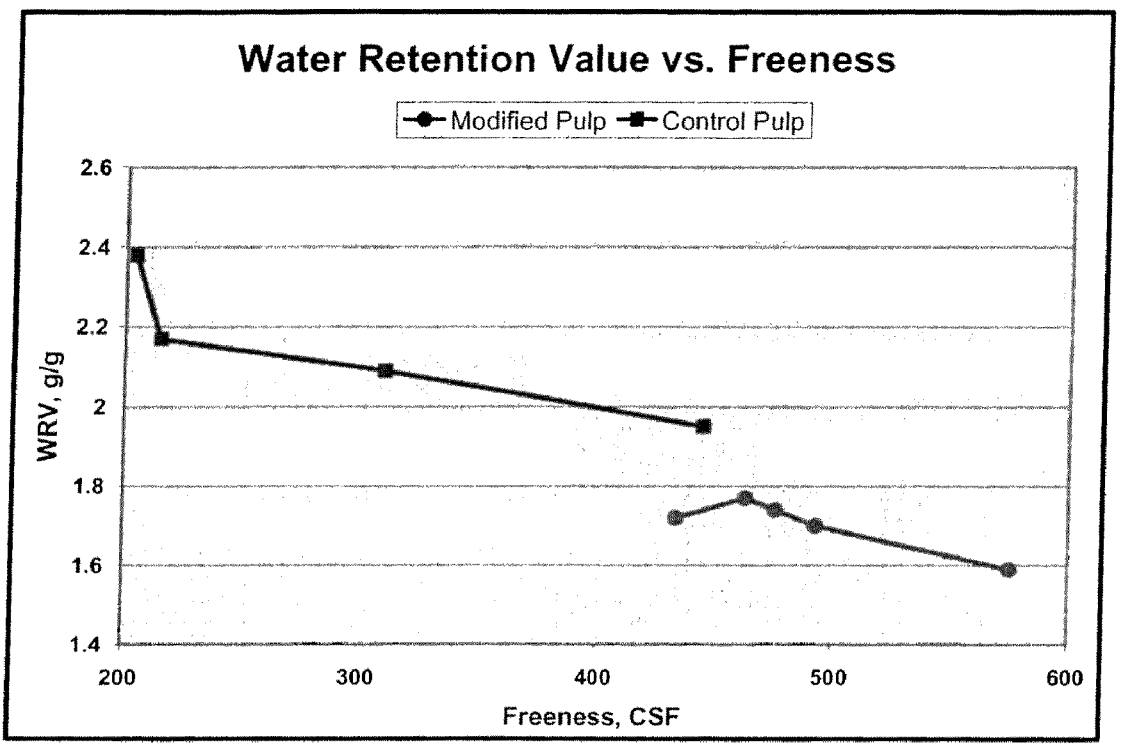
FIG. 3 is a plot of bulk versus Sheffield Smoothness for the modified pulp of this invention and the same unmodified pulp.

The results are set forth in Table IV below and in FIGS. 2 and 3.

TABLE IV

|  | Freeness, csf | Water Retention Value, g/g | Bulk, cc/g | Sheffield Smoothness |
|---|---|---|---|---|
| Modified Pulp | 575 (unrefined) | 1.59 | 2.04 | 296 |
|  | 558 | — | 1.88 | 256 |
|  | 493 | 1.7 | 1.76 | 238 |
|  | 476 | 1.74 | 1.76 | 225 |
|  | 463 | 1.77 | 1.70 | 221 |
|  | 432 | 1.72 | 1.67 | 212 |
| Control Pulp | 445 (unrefined) | 1.95 | 1.60 | 216 |
|  | 315 | 2.09 | 1.52 | 186 |
|  | 220 | 2.17 | 1.49 | 136 |
|  | 206 | 2.38 | 1.51 | 122 |

Freeness and water retention values are indications of paper drainage and dewatering. As shown in FIG. 2, the data shows that the modified pulp may be dewatered and dried faster on paper-machine than the unmodified pulp. The data also demonstrates that the paper bulk is significantly improved. As shown in FIG. 3, this is even true when comparing the bulk increase at the same smoothness of paper.

Example 3

Modified Kraft pulp was also made from Southern Pine chips. Like the hardwood case, significant bleaching savings was obtained. Table V below indicates the reduced fiber coarseness of the modified pulp vs. the control pulp at the same kappa number of 26. The test was done by Kajaani FiberLab tester.

TABLE V

|  | Modified Pine | Control pine |
|---|---|---|
| Fiber Coarseness, mg/100 m | 26.1 | 29.2 |

Example 4

Bleached southern hardwood Kraft pulp was treated with NaOH solution (the concentration of NaOH being 5% based on the total system of pulp and water) at ambient temperature for 15 minutes. This is an alternative way of extracting hemicelluloses from the fibers. The pulp was then thoroughly washed with water, and made into Tappi hand-sheets. Paper bulk of paper formed from the modified pulp was 2.03 cc/g, while the control paper bulk was 1.85 cc/g. The brightness was also increased from the control of ISO 86.4 to the modified pulp of ISO 89.2.

What is claimed is:

1. A method of producing a modified Kraft pulp comprising:
    treating wood chips with an acidic solution in an extraction process with steam, a liquid comprising water or a combination thereof to remove 5% to 20% hemicellulose to form treated wood chips under acidic condition; and
    subjecting the treated wood chips to Kraft pulping to form a modified Kraft pulp wherein the amount of hemicellulose contained in the modified Kraft pulp is from more than 5% to less than or equal to 10% by oven dried weight of the modified Kraft pulp; wherein, prior to or during the extraction process, the wood chips are treated with a composition comprising at least one peroxide at an acid pH wherein the peroxide is not peroxymonosulfuric acid or salts thereof (OXONE).

2. The method of claim 1 further comprising a washing step.

3. The method of claim 1 further comprising a refining step.

4. The method of claim 1 wherein the wood chips are extracted at temperatures ranging from 140° C. to 160° C.

5. The method of claim 1 wherein the wood chips are extracted at treatment time ranging from 30 minutes to 240 minutes.

6. The method of claim 1 wherein the amount of hemicellulose contained in the modified Kraft pulp is from about 6% to about 8% by oven dried weight of the modified Kraft pulp.

7. The method of claim 1 wherein the extraction step produces a modified Kraft pulp having from about 2% to about 8% less hemicelluloses than the same Kraft pulp when unmodified.

8. The method of claim 1 wherein, prior to or during the extraction process, the wood chips are treated with a composition comprising a peroxide and a transition metal catalyst.

9. The method of claim 1 wherein an additional peroxide is added to an extracted hemicellulose portion after the treating step.

10. The method of claim 1 wherein the peroxide is at least one member selected from the group consisting of hydrogen peroxide, perborate, per carbonate, persulfate, or peracetic acid.

11. The method of claim 1 wherein the pH of the extraction step is less than about 6.

12. The method of claim 1 wherein the pH of the extraction step ranges from about 2 to about 4.

13. The method of claim 1 wherein, prior to or during the extraction process, the wood chips are treated with a composition comprising a peroxide and at least one transition metal catalyst selected from the group consisting of iron, copper, manganese, and cobalt salts.

14. The method of claim 1, wherein the removed hemicellulose is a) burned as a fuel, b) fermented to produce fuel chemicals, c) added to the wet end of a papermaking process, d) added to the size press or coater of a papermaking process, or e) any one or more of a)-d).

15. The method of claim 1, further comprising producing fuel chemicals from the removed hemicellulose.

16. The method of claim 1, further comprising producing fuel chemicals from the removed hemicellulose, wherein the fuel chemicals comprise ethanol.

* * * * *